United States Patent [19]

Michalos

[11] Patent Number: 5,569,224
[45] Date of Patent: Oct. 29, 1996

[54] EYEDROP APPLICATOR

[76] Inventor: Peter Michalos, 137 Hampton Rd., South Hampton, N.Y. 11968

[21] Appl. No.: 460,779

[22] Filed: Jun. 2, 1995

[51] Int. Cl.$^6$ ............................ A61M 35/00; A61H 33/04
[52] U.S. Cl. ............................................ 604/300; 604/302
[58] Field of Search ................................. 604/294, 295, 604/300, 301, 302; 2/13, 449

[56] References Cited

U.S. PATENT DOCUMENTS

| | | | |
|---|---|---|---|
| 3,058,466 | 10/1962 | Routsong | 604/302 |
| 3,446,209 | 5/1969 | Macha | 128/233 |
| 4,183,355 | 1/1980 | Meckler | 604/302 |
| 4,468,103 | 8/1984 | Meckler | 604/300 |
| 4,531,944 | 7/1985 | Bechtle | 604/302 |
| 4,726,075 | 2/1988 | Hinrichs | 2/13 |
| 5,059,188 | 10/1991 | Goddard | 604/300 |
| 5,154,710 | 10/1992 | Williams . | |
| 5,255,024 | 10/1993 | Jensen | 604/300 |

*Primary Examiner*—John G. Weiss
*Assistant Examiner*—David J. Cho
*Attorney, Agent, or Firm*—Jerome D. Jackson

[57] ABSTRACT

A frame assembly for accurate placement of eyedrops. The assembly includes opaque eye plates located to be in front of the wearers eyes. Each eye plate defines a liquid aperture and an optical aperture above the liquid aperture. The assembly also includes two funnels, each having an aperture aligned with one of the liquid apertures.

13 Claims, 3 Drawing Sheets

5,569,224

EYEDROP APPLICATOR

BACKGROUND OF THE INVENTION

1. Field of the Invention

This invention relates generally to a device for applying eyedrops to human eyes and, more particularly, to a frame assembly having opaque eye plates with a liquid aperture and an optical aperture in each eye plate.

1. Description of Related Art

Placement of eyedrops can be challenging, especially for people having certain conditions such as Arthritis or Parkinson's disease. Some conventional methods of applying eyedrops can result in misapplication of the eyedrops and the risk of poking the eye and scratching the cornea.

SUMMARY OF THE INVENTION

It is an object of the present invention to provide an eyedrop applicator that allows efficient application of medications.

To achieve this and other objects of the present invention, a frame assembly comprises a left eye plate having a first major surface defining a first optical aperture and a first liquid aperture, the first major surface being opaque; a right eye plate, coupled to the left eye plate, having a second major surface defining a second optical aperture and a second liquid aperture, the second major surface being opaque; and securing means, coupled to the left eye plate and to the right eye plate, for securing the left and right eye plates to a person's head.

According to another aspect of the present invention, a frame assembly comprises a left eye plate having a first major surface defining a first optical aperture and a first liquid aperture, the first major surface being opaque; a first arm, coupled to the left eye plate at a first point, the first arm extending in a direction transverse to the first major surface; a right eye plate, coupled to the left eye plate, having a second major surface defining a second optical aperture and a second liquid aperture, the second major surface being opaque; a second arm, coupled to the right eye plate and a second point, the second arm extending in a direction transverse to the second major surface, wherein and the first optical aperture and the first liquid aperture define a line perpendicular to a line defined by the first and second points, and the second optical aperture and the second liquid aperture define a line perpendicular to the line defined by the first and second points.

According to yet another aspect of the present invention, a method of applying eyedrops using a frame assembly having a left eye plate having a first major surface defining a first optical aperture and a first liquid aperture, the first major surface being opaque, and a right eye plate, coupled to the left eye plate, having a second major surface defining a second optical aperture and a second liquid aperture, the second major surface being opaque, the method comprising the steps of securing the left and right eye plates to a person's head; passing a drop of a medication through the first liquid aperature, while looking into the first optical aperature; and passing a drop of the medication through the second liquid aperature, whild looking into the second optical aperature.

The accompanying drawings which are incorporated in and which constitute a part of this specification, illustrate embodiments of the invention and, together with the description, explain the principles of the invention, and additional advantages thereof.

DESCRIPTION OF THE PREFERRED EMBODIMENT

Figure 1:
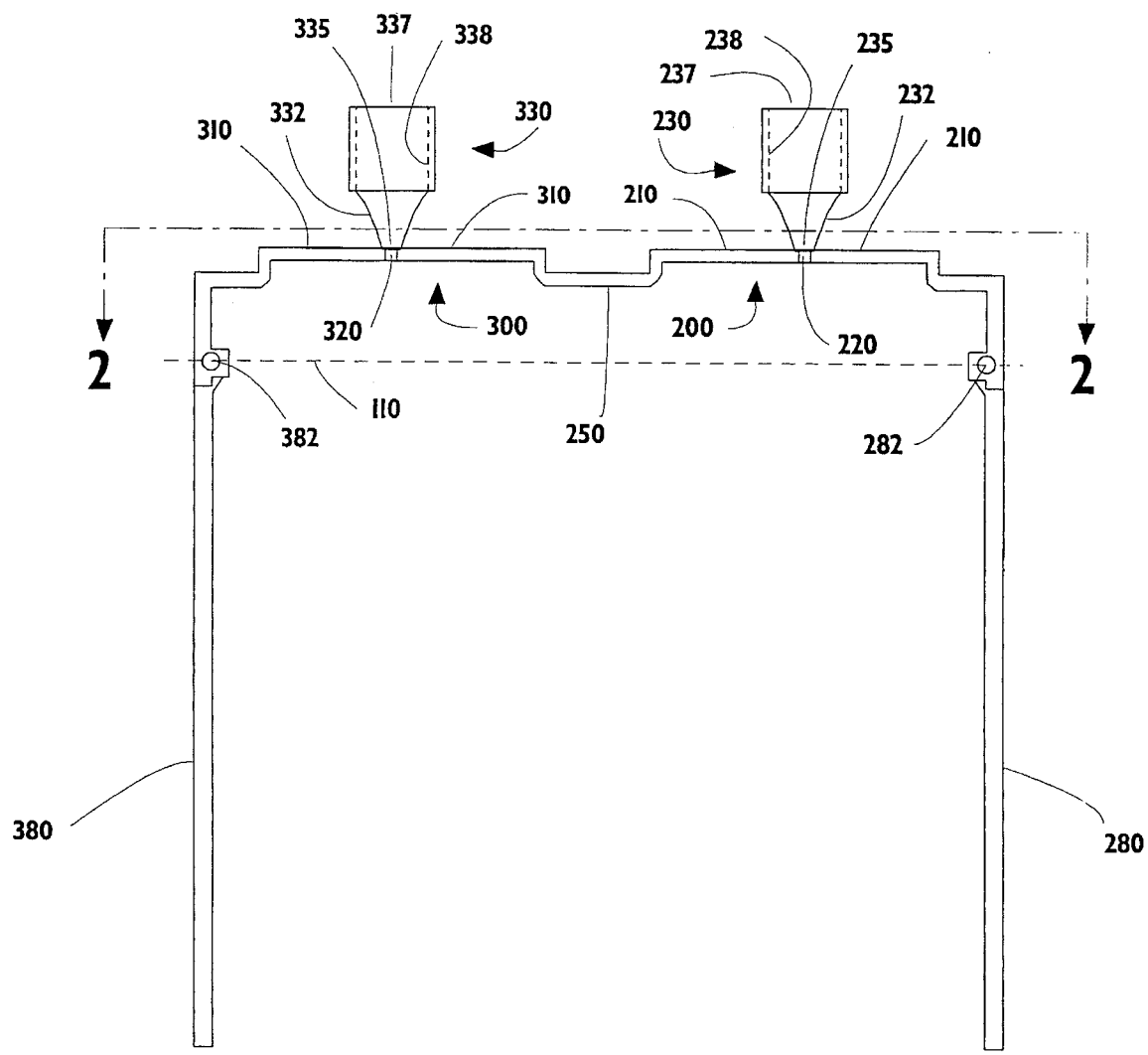
FIG. 1 is a bottom view of an eye frame assembly for applying eyedrops, according to a preferred embodiment of the present invention.
Figure 2:
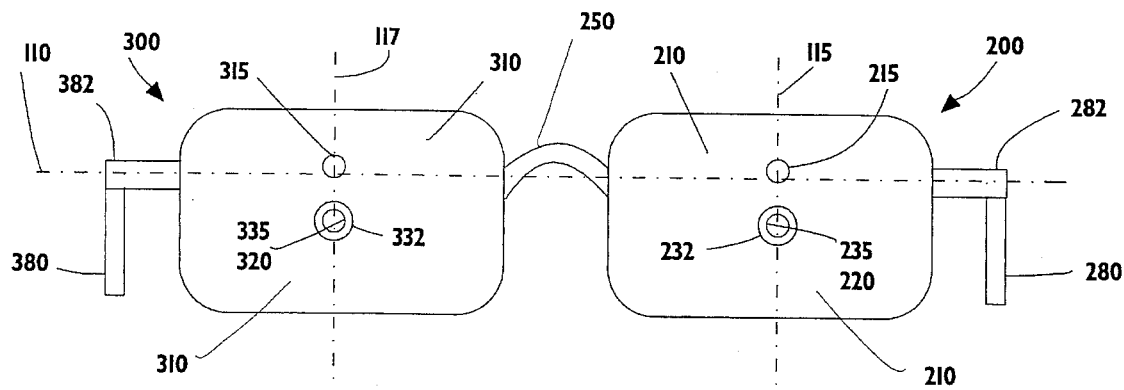
FIG. 2 is a front view of the eye frame assembly shown in FIG. 1.

FIG. 1 shows a bottom view of frame assembly 100 according to a preferred embodiment of the present invention, and FIG. 2 is a front view of frame assembly 100 taken along the line 2—2 shown in FIG. 1. Frame assembly 100 includes an opaque eye plate 200 having an opaque major surface 210, and an opaque eye plate 300 having an opaque major surface 310. A nose bridge 250 couples eye plate 200 to eye plate 300. A hinge 282 couples left arm 280 to eye plate 200. Left arm 280 extends away from opaque surface 210 in a direction transverse to opaque surface 210. A hinge 382 couples right arm 380 to eye plate 300. Right arm 380 extends away from opaque surface 310 in a direction transverse to opaque surface 310. Hinges 282 and 382 defined a line 110 shown in FIGS. 1 and 2.

The combination of left arm 280 and right arm 380 acts to secure eye plates 200 and 300 to a person's head.

Figure 3:
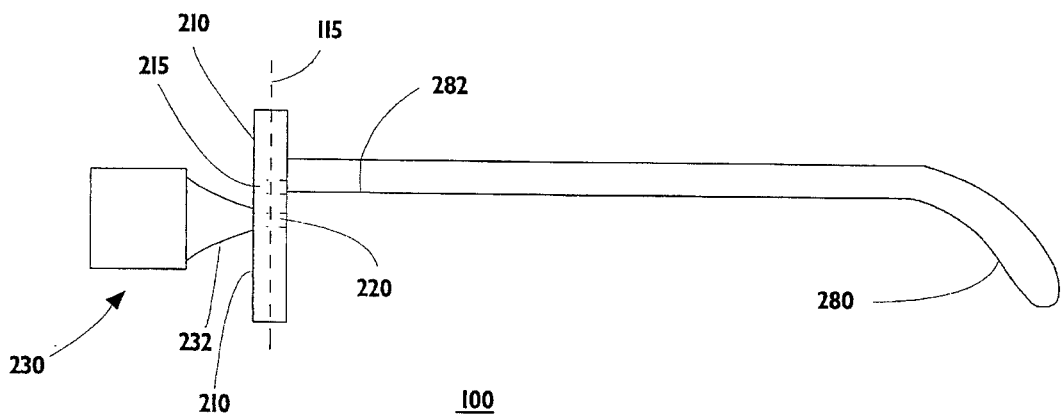
FIG. 3 is a side view of the eye frame assembly shown in FIG. 1.

FIG. 3 is a side view of the preferred frame assembly.

Opaque surface 210 defines an optical aperture 215 and a liquid aperture 220. Liquid aperture 220 has a diameter of 5 mm, which is slightly wider than the tip of a typical eyedrop bottle. Liquid aperture 220 is in the center of opaque surface 210. Optical aperture 215 is a through hole defined by opaque surface 210. Optical aperture 215 and liquid aperture 220 are separated by a distance of 8 millimeters, and define a line 115 shown in FIGS. 2 and 3. Line 115 is perpendicular to line 110. Thus, as shown in FIG. 2, optical aperture 215 and the liquid aperture 220 define a line 115 transverse to a line defined by optical aperture 215 and optical aperture 315.

Similarly, opaque surface 310 defines an optical aperture 315 and a liquid aperture 320. Liquid aperture 320 has a diameter of 5 mm. Liquid aperture 320 is in the center of opaque surface 310. Optical aperture 315 is a through hole defined by opaque surface 310. Optical aperture 315 and liquid aperture 320 are separated by a distance of 8 millimeters, and define a line 117 shown in FIG. 2. Line 117 is perpendicular to line 110. Thus, as shown in FIG. 2, optical aperture 315 and the loquid aperture 320 define a line 117 transverse to a line defined by optical aperture 215 optical aperture 315.

Because eye plate surface 210 is opaque, optical aperture 215 is a prominent optical target for the wearer of frame assembly 100. Similarly, because eye plate surface 310 is opaque, optical aperture 315 is a prominent optical target for the wearer of frame assembly 100.

Optical aperture 215 in left eye plate 200 is separated from optical aperture 315 in right eye plate 300 by a distance of 60 to 80 millimeters.

Funnel 230 has a tapered end 232 attached to the center of opaque surface 210. Funnel 230 defines an aperture 235 aligned with liquid aperture 220 of surface 210, and an aperture 237. In other words, tapered end 232 is attached to surface 210 at points around liquid aperture 220. Funnel 230 defines an inner, threaded surface 238. Funnel 230 is integrally formed with eyeplate 200. This integral formation may be achieved with injection molding.

Similarly, funnel 330 has a tapered end 332 attached to the center of opaque surface 310. Funnel 330 defines an aperture 335 aligned with liquid aperture 320 of surface 310, and an aperture 337. Funnel 330 defines an inner, threaded surface 338. Funnel 230 is integrally formed with eyeplate 200.

Each of funnels 230 and 330 acts to support and align an eyedrop bottle.

To apply eyedrops using the preferred frame assembly 100, a person puts on frame assembly 100 as one would put on a pair of eyeglasses, screws an eyedrop bottle into funnel 230, tilts his or her head back, looks through optical aperture 215 with the left eye, and squeezes the eyedrop bottle. Following this procedure causes a drop to fall into the lower corneal area of the left eye near the lower eye lid. The normal blinking reflex is reduced because the eye is oriented toward optical aperture 215, not liquid aperture 220. Subsequently, the person screws the eyedrop bottle into funnel 330, looks through optical aperture 315 with the right eye, and squeezes the eyedrop bottle. In other words, the person passes a drop of a medication through the liquid aperture 220, while looking into optical aperture 215, and then passes a drop of the medication through liquid aperture 320, while looking into optical aperture 315.

Figure 4:
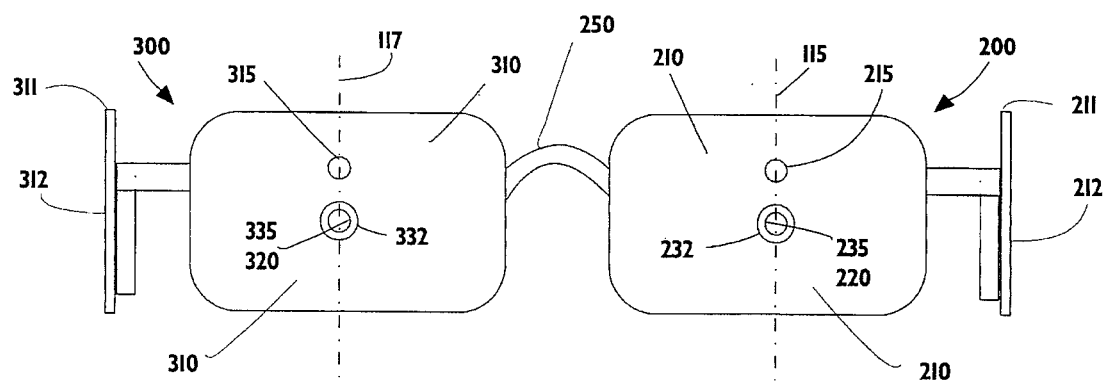
FIG. 4 is a front view of the a preferred eye frame assembly in accordance with an alternative embodiment of the present invention.
Figure 5:
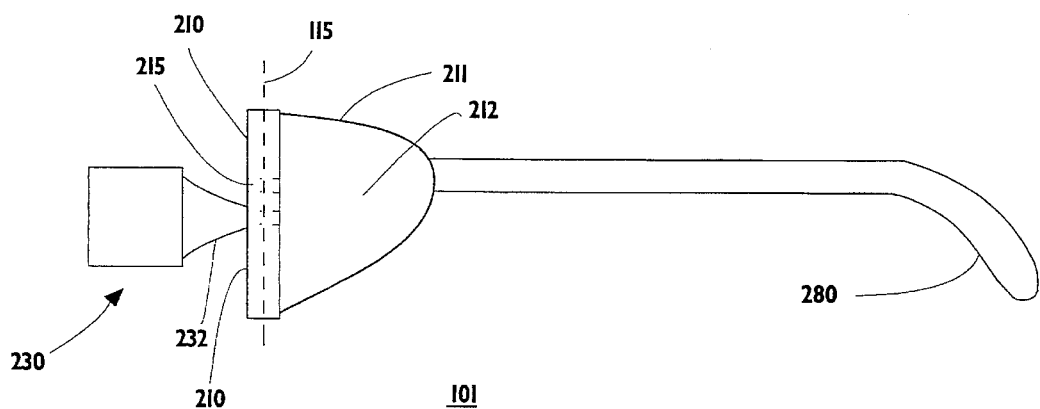
FIG. 5 is a side view of the eye frame assembly shown in FIG. 4.

FIGS. 4 and 5 show a frame assembly 101 according to an alternate embodiment of the present invention. In FIGS. 4 and 5, elements corresponding to elements of frame assembly 100 are labeled with corresponding reference numbers. Frame assembly 200 is similar to frame assembly 100, except that frame assembly 101 includes opaque side plate 211 attached to eye plate 200, and opaque side plate 311 attached to eye plate 300. Side plate 211 has opaque major surface 212 extending in a direction transverse to major surface 210, and side plate 311 has opaque major surface 312 extending in a direction transverse to major surface 310. Opaque side plates 211 and 311 further shield the eye from ambient light, making optical apertures 215 and 315 more prominent, and further reducing the normal blink reflex.

Thus, the preferred frame assemblies allow accurate application of eyedrops. The narrow liquid apertures in the eye plates act to space an eyedrop bottle away from the eye, reducing the possibility of the dropper tip touching the eye, and therefore reducing the possibility of infection. Further, because the eye plate surfaces are opaque, reducing the blink reflex, the possibility of misapplication of the drops, with the resulting waste of medicine, is reduced.

Additional advantages and modifications will readily occur to those skilled in the art. The invention in its broader aspects is therefore not limited to the specific details, representative apparatus, and illustrative examples shown and described. Accordingly, departures may be made from such details without departing from the spirit or the scope of applicants general inventive concept. The invention is defined in the following claims.

What is claimed is:

1. A frame assembly for wearing on the head of a person, the top of the person's head defining an up direction, the frame assembly comprising:

a left eye plate having a first opaque major surface defining a first optical aperture and a first liquid aperture;

a right eye plate, coupled to the left eye plate, having a second opaque major surface defining a second optical aperture and a second liquid aperture, the first optical aperture and the first liquid aperture defining a line transverse to a line defined by the first and second optical apertures, and the second optical aperture and the second liquid aperture defining a line transverse to the line defined by the first and second optical apertures; and securing means, coupled to the left eye plate and to the right eye plate, for securing the left and right eye plates to the person's head such that the first optical aperture is above the first liquid aperture and the second optical aperture is above the second liquid aperture.

2. The frame assembly of claim 1 further including a left support member, coupled to the first major surface around the first liquid aperture, the left support member extending away from the first major surface; and a right support member, coupled to the second major surface around the second liquid aperture, the right support member extending away from the second major surface.

3. The frame assembly of claim 1 further including a left funnel defining a left funnel aperture aligned with the first liquid aperture; and a right funnel defining a right funnel aperture aligned with the second liquid aperture.

4. The frame assembly of claim 1 further including a left funnel defining a left funnel aperture aligned with the first liquid aperture, the left funnel being integrally formed with the left eye plate; and a right funnel defining a right funnel aperture aligned with the second liquid aperture, the right funnel being integrally formed with the right eye plate.

5. The frame assembly of claim 1 further including a left funnel defining a left funnel aperture aligned with the first liquid aperture, the left funnel defining an inner threaded surface; and a right funnel defining a right funnel aperture aligned with the second liquid aperture, the right funnel defining an inner threaded surface.

6. The frame assembly of claim 1 further including a left side plate, coupled to the left eye plate, the left side plate defining a left major surface extending in a direction transverse to the first major surface, the left major surface being opaque; and a right side plate, coupled to the right eye plate, the right side plate defining a right major surface extending in a direction transverse to the second major surface, the right major surface being opaque.

7. A frame assembly for wearing on the head of a person, the top of the person's head defining an up direction, the frame assembly comprising:

a left eye plate having a first opaque major surface defining a first optical aperture and a first liquid aperture;

a first arm, coupled to the left eye plate, the first arm extending in a direction transverse to the first major surface;

a right eye plate, coupled to the left eye plate, having a second opaque major surface defining a second optical aperture and a second liquid aperture, the first optical aperture and the first liquid aperture defining a line transverse to a line defined by the first and second optical apertures, and the second optical aperture and the second liquid aperture defining a line transverse to the line defined by the first and second optical apertures;

a second arm, coupled to the right eye plate, the second arm extending in a direction transverse to the second major surface, wherein the left eye plate, right eye plate, and first and second arms are configured such that the first optical aperture is above the first liquid aperture and the second optical aperture is above the second liquid aperture when the frame assembly is worn.

8. The frame assembly of claim 7 further including a left side plate, coupled to the left eye plate, the left side plate defining a left major surface extending in a direction transverse to the first major surface, the left major surface being opaque; and a right side plate, coupled to the right eye plate, the right side plate defining a right major surface extending in a direction transverse to the second major surface, the right major surface being opaque.

9. The frame assembly of claim 1 further including a left support member, coupled to the first major surface around the first liquid aperture, the left support member extending away from the first major surface; and a right support member, coupled to the second major surface around the second liquid aperture, the right support member extending away from the second major surface.

10. The frame assembly of claim 7 further including a left funnel defining a left funnel aperture aligned with the first liquid aperture; and a right funnel defining a right funnel aperture aligned with the second liquid aperture.

11. The frame assembly of claim 7 further including a left funnel defining a left funnel aperture aligned with the first liquid aperture, the left funnel being integrally formed with the left eye plate; and a right funnel defining a right funnel aperture aligned with the second liquid aperture, the right funnel being integrally formed with the right eye plate.

12. The frame assembly of claim 7 further including a left funnel defining a left funnel aperture aligned with the first liquid aperture, the left funnel defining an inner threaded surface; and a right funnel defining a right funnel aperture aligned with the second liquid aperture, the right funnel defining an inner threaded surface.

13. A method of applying eyedrops using a frame assembly having a left eye plate having a first opaque major surface defining a first optical aperture and a first liquid aperture, and a right eye plate, coupled to the left eye plate, having a second opaque major surface defining a second optical aperture and a second liquid aperture, the first optical aperture and the first liquid aperture defining a line transverse to a line defined by the first and second optical apertures, and the second optical aperture and the second liquid aperture defining a line transverse to the line defined by the first and second optical apertures, the method comprising the steps of passing a drop of a medication through the first liquid aperture into the lower corneal area of the left eye, while looking into the first optical aperture; and passing a drop of the medication through the second liquid aperture into the lower corneal area of the right eye, while looking into the second optical aperture.

* * * * *